United States Patent [19]

Ueno et al.

[11] Patent Number: 5,756,363
[45] Date of Patent: May 26, 1998

US005756363A

[54] LIPOSOME REAGENT FOR IMMUNOAGGLUTINATION AND IMMUNOANALYTICAL METHOD

[75] Inventors: Takahisa Ueno; Mamoru Umeda; Hideaki Shibata, all of Ibaraki, Japan

[73] Assignee: Nissui Pharmaceutical Co., Ltd., Japan

[21] Appl. No.: 464,866

[22] PCT Filed: Feb. 1, 1994

[86] PCT No.: PCT/JP94/00136

§ 371 Date: Jul. 14, 1995

§ 102(e) Date: Jul. 14, 1995

[87] PCT Pub. No.: WO94/18567

PCT Pub. Date: Aug. 18, 1994

[30] Foreign Application Priority Data

Feb. 3, 1993 [JP] Japan ................... 5-016167

[51] Int. Cl.$^6$ .................................. G01N 33/544
[52] U.S. Cl. .......................... 436/528; 436/518; 436/529; 436/530; 436/531; 436/532; 436/533; 436/534; 436/829; 435/5; 435/7.1
[58] Field of Search ................ 436/528, 529, 436/531, 532, 533, 534, 829, 518, 530; 435/5, 7.1

[56] References Cited

U.S. PATENT DOCUMENTS

| | | | |
|---|---|---|---|
| 4,598,051 | 7/1986 | Papahadjopoulos et al. | 436/512 |
| 4,762,915 | 8/1988 | Kung et al. | 530/405 |
| 5,000,960 | 3/1991 | Wallach | 424/450 |

FOREIGN PATENT DOCUMENTS

| | | |
|---|---|---|
| 63-201568 | 8/1988 | Japan . |
| 63-201568 A | 8/1988 | Japan . |
| 63-274870 | 11/1988 | Japan . |
| 63-274870 A | 11/1988 | Japan . |

OTHER PUBLICATIONS

"Large Liposome Agglutination Technqiue for the Serological Detection of Syphilis," Viola T. Kung et al., Journal of Immunological Methods vol. 90 1986, pp. 189–196.

"Antibody Induced Agglutination of Galactocerebroside Liposomes," Debi P. Sarkar et al., Indian Journal of Experimental Biology vol. 20 Jul. 1982, pp. 522–524.

*Primary Examiner*—Jeffrey Stucker
*Attorney, Agent, or Firm*—Lorusso & Loud

[57] ABSTRACT

An immunoagglutination reagent includes liposomes, as a carrier, with a covalently bound antigen or antibody immobilized thereon. The reagent is used to assay an antibody or an antigen on the basis of agglutination. The assaying can be done at a high sensitivity in the short wave region where the change in turbidity caused by the agglutination is enhanced. An antibody or an antigen is immobilized onto the surface of the liposome, and a water-soluble polymer compound or a gelled compound is entrapped in the liposomes. The substance entrapped in the immunoagglutination reagent enhances the change in turbidity via the agglutination caused by the antigen-antibody reaction.

6 Claims, 2 Drawing Sheets

—●— Standard curve according to Example 1
—□— Standard curve according to comparative Example 1

—○— Standard curve according to Example 1

—●— Standard curve according to comparative Example 1

LIPOSOME REAGENT FOR IMMUNOAGGLUTINATION AND IMMUNOANALYTICAL METHOD

This application is a 371 continuation of PCT/JP94/00136.

BACKGROUND OF THE INVENTION

1. Field of the Invention

The present invention relates to an immunoagglutination reagent. More specifically, the present invention relates to an immunoagglutination reagent capable of assaying a wide concentration range of a substance present in a sample, with high sensitivity, by a simple procedure or by using an automatic analyzer. The present invention also relates to an immunoanalytical method using the same.

2. Background Art

Immunoanalytical methods using an antigen-antibody reaction are extremely important in clinical diagnosis of endocrine diseases and the like. A variety of immunoanalytical methods have become conventional.

Among these conventional methods is an immunoanalytical method comprising reacting an antibody or an antigenic substance in a sample with an immunoagglutination reagent comprising an antigenic substance or an antibody bound to a carrier, measuring the agglutination level caused by the antigen-antibody reaction using the naked eye or as turbidity using a spectrophotometer, comparing the results with a standard curve and thereby obtaining a value for the antibody or the antigenic substance contained in the sample. Synthetic latex particles such as polystyrene have primarily been used as the carrier in such immunoanalytical methods.

Because the surface of the immunoagglutination reagent using such conventional synthetic latex particles as the carrier is hydrophobic, agglutination via hydrophobic binding readily occurs in an aqueous solution of pH 7 to 7.5, suitable for antigen-antibody reaction. Thus, such a reagent tends to induce non-specific agglutination. Therefore, the assay precision is likely to vary. Thus, patent applications (for example, Japanese Patent Publication No. Hei 3-142360 and Japanese Patent Publication No. Hei 3-76425) have been directed to techniques for adding additives to immunoagglutination reagents bound to synthetic latex particles as the carrier so as to suppress such non-specific agglutination.

Because an antigen or an antibody is immobilized via physical adsorption onto synthetic latex particles, the antigen or the antibody, in long-term storage, dissociates from the synthetic latex particles, causing a decrease in assay sensitivity.

More recently, such latex agglutination reagents have been used in general purpose biochemical automatic analyzers, to assay an antigen or an antibody in a sample. However, such use encounters the problem that an immunoagglutination reagent using the synthetic latex particles as a carrier adheres to the reaction cells of the automatic analyzer, thereby adversely affecting the assay precision.

So as to overcome these problems, the present inventors have developed a liposome agglutination reagent using a liposome as the carrier. The liposome is covalently coated with an antigen or an antibody. See Japanese Patent Application No. Hei 4-164783. Because an antigen or an antibody is covalently bound onto the surface of the liposome in the liposome agglutination reagent, the antigen or the antibody does not dissociate from the liposomes even after a long-term storage. Because the surface of liposome of itself is hydrophilic, agglutination via hydrophobic binding and, therefore, non-specific agglutination hardly occurs.

The reagent also offers the advantage that the reaction cells of an automatic analyzer do not become contaminated, which advantage has never been offered by a conventional latex agglutination reagent.

Because latex agglutination reagents themselves have high turbidities, i.e., because the blank reading for the reagent itself is high, such reagents should be used for assay with a spectrophotometer in the long wave region due to the smaller change in turbidity. Hence, improvement in the sensitivity thereof has been very difficult. Alternatively, due to the lower refractive index, the liposome agglutination reagent can be used for assay in the short wave region, i.e., about 34 nm, where the change in turbidity is observed as a larger value.

However, liposomes have a refractive index close to that of water. Additionally, liposomes are prepared in an aqueous solution and, therefore, aqueous solution is entrapped in the liposomes. Hence, almost no difference in refractive index is observed between the aqueous solution entrapped in the liposome and the external aqueous phase. Although the liposome agglutination reagent offers the advantages that turbidity is not increased even when the liposomes themselves become agglutinated and that the sample can be assayed at a short wave length of 340 nm, use of the liposome agglutination reagent encounters the problem that the assay sensitivity of the reagent is low, regardless of whether it is used with a spectrophotometer, an automatic analyzer or the naked eye.

SUMMARY OF THE INVENTION

Thus, overcoming such problems involved in assay with the liposome agglutination reagent, i.e., an antigen or an antibody covalently bonded onto a liposome, is the objective of the present invention. In other words, the first objective of the present invention is to provide an immunoagglutination reagent capable of a highly sensitive assay in the shortwave range where the change in turbidity via agglutination can be distinctively observed.

Another objective of the present invention is to provide a highly sensitive immunoagglutination reagent based on liposomes with a higher refractive index.

A further objective of the present invention is to provide an immunoanalytical method having a high sensitivity, even when the sample has a low concentration of the substance to be assayed.

To overcome the problems described above, the present invention provides an immunoagglutination reagent for an assay by agglutination through an antigen-antibody reaction wherein liposomes are used as the carrier of the immunoagglutination reagent, an antibody or an antigen being immobilized on the surface of the liposomes, and wherein the liposomes contain an entrapped water-soluble polymer or a gelled compound.

In accordance with the present invention, the liposomes may be made of any conventional liposome material containing phospholipid and cholesterol as the principal components thereof. The size of the liposomes may be 50 nm to 5 μm, more preferably 100 to 600 nm, and most preferably 100 to 200 nm. In the foregoing range, the reagent is very stable and the liposomes hardly precipitate during storage. Accordingly, the reagent may be suitably used for measuring the turbidity with a spectrophotometer in a slide agglutination method or the like.

The water-soluble polymer compound or the gelled compound entrapped in the liposomes of the immunoagglutination reagent in accordance with the present invention may be a polymer or a copolymer such as acrylamide, glycosylmethacrylate and the like; cellulose or a derivative thereof; a methacrylate polymer; a polymer or a copolymer of acrylic acid or an acrylate; a polymer of N-vinylpyrollidone; and the like. These water-soluble polymer compounds or polymers should be crosslinked via a crosslinking agent.

The immunoagglutination reagent in accordance with the present invention is produced by immobilizing an antibody or an antigen, for example, via covalent bonding, onto the surface of liposome as described below. In accordance with the present invention, however, the immunoagglutination reagent comprises liposomes entrapping therein a water-soluble polymer compound or a gelled compound, with no specific limitation to the bond between the antibody or antigen and the surface of the liposomes. For example, the periodate process, the passive process and like conventional techniques may be used for the bonding of the antibody or antigen to the liposomes.

The preparation of liposomes from phospholipid, cholesterol, and phospholipid introduced with a crosslinking agent, by the Vortexing process or a process using glass beads will first be described.

The crosslinking agent used in the process, may be, for example, N-hydroxysuccinimidyl-3-(2pyridyldithio) propionate (SPDP), N-succinimidyl-4-(p-maleimide phenyl)butyrate (SMPB), N-succinimidyl-4-(p-maleimide phenyl) acetate (SMPA), N-succinimidyl-4-(p-maleimide phenyl)propionate (SMPP), N-(γ-maleimide butyryloxy) succinimide (GMBS) and N-(ε-maleimide caproyloxy) succinimide (EMCS) and the like.

The solvents contained in admixture with the phospholipid, cholesterol or phospholipid modified with a crosslinking agent are distilled off under aspiration. Subsequently, by adding an aqueous solution of a polymerizable monomer into a flask with a thin film formed on the wall surface thereof, by further adding glass beads if necessary, and shaking the flask after sealing, a liposome suspension is prepared. By thereafter passing the suspension through a polycarbonate film of a given pore size, liposomes having a uniform particle size and entrapping the polymerizable monomer therein can be recovered. After removing the polymerizable monomer not entrapped in the liposomes from the external solution by dialysis, the monomer entrapped in liposomes should be polymerized using a polymerization initiator.

A group reactive with the crosslinking agent should be introduced into the molecule of the antibody or antigen. Mixing and reacting the thus prepared liposomes with the modified antibody or the modified antigen in a buffer solution, the antibody or antigen become immobilized on the surface of the liposomes.

The antibody immobilized onto the liposome surface in accordance with the present invention, may be a monoclonal antibody and/or a polyclonal antibody recognizing the antigenic substance to be assayed. The immunoagglutination reagents comprising a combination of such antibody and liposomes are grouped into the following types: an immunoagglutination reagent wherein only a monoclonal antibody is immobilized on the liposome surface; an immunoagglutination reagent wherein only a polyclonal antibody is immobilized on the liposome surface; an immunoagglutination reagent wherein both a monoclonal antibody and a polyclonal antibody are immobilized on the same liposome surface; and an immunoagglutination reagent comprising a mixture of a monoclonal antibody immobilized on the surfaces of one portion of the liposomes and a polyclonal antibody immobilized on the surfaces of another portion of the liposomes.

In the immunoagglutination reagent comprising a combination of a monoclonal antibody and a polyclonal antibody as described above, a monoclonal antibody with higher affinity for an antigen complements the lower affinity of a polyclonal antibody whereas use of a polyclonal antibody with higher agglutination potency avoids the laborious work in selecting a combination of monoclonal antibodies.

As the antibody immobilized onto the liposome surface, use may be made of the IgG fraction, or otherwise, use may be made of one fragment thereof, i.e., the $F(ab')_2$ fragment. In accordance with the present invention, the antigen to be immobilized onto the liposome surface may be a plasma protein, a virus protein or the like.

The antigenic substances which may be assayed by the immunoanalytical method with the immunoagglutination reagent in accordance with the present invention, include hormones (for example, insulin, HCG-β, growth hormone, TSH, LH, FSH, prolactin, thyroxine, triiodothyronine, gastrin, glucagon, somatostatin, etc.); enzymes (for example, elastase, amylase, protease, lipase, ribonuclease, enolase, alkaliphosphatase, etc.); serum proteins (for example, IgG, IgA, IgM, IgE, IgD, RF, SLO, macroglobulin, TBG, sugar proteins, lipopolysaccharides, apo-AI, AII, B, CI, CII, CIII, Proteins D, E, F, etc.); tumor-related antigens (for example, CEA, α-fetoprotein, ferritin, POA, CA19-9, CA125, etc.); DNA binding proteinous factors; cytokines (for example, interferon, interleukin-1, interleukin-2, etc.); a variety of bacteria, viruses, protozoa (for example, fungus, streptococcus, hepatitis virus, herpes virus, HIV virus, Troxoplasma gondii, Plasmodium, Entamoeba histolytica, etc.); and the like. The present invention is particularly suitable for assay of serum proteins, tumor-related antigens and viruses, which assays typically involve a great number of samples assayed together within a short period of time.

Antibodies which may be assayed include, for example, antibodies against viruses (for example, HIV, ATL, HB, etc.), antinuclear factor and the like.

In a immunoanalytical method using the immunoagglutination reagent in accordance with the present invention, a sample containing a subject substance should be assayed, for example, as follows. Firstly, the immunoagglutnation reagent is mixed with a sample containing a subject substance in an appropriate buffer (for example, TES buffer), thereby inducing an antigen-antibody reaction whereby liposomes are agglutinated. The decrease in photo-transmission, depending on the level of the agglutination, should be analyzed with a spectrophotometer or an automatic analyzer (HITACHI TYPE 705, 7050, 7150, 736, 7070, etc.). Then, comparing the decrease with a standard curve, an assay value for the subject substance is obtained.

BEST EMBODIMENTS FOR CARRYING OUT THE INVENTION

Figure 1:
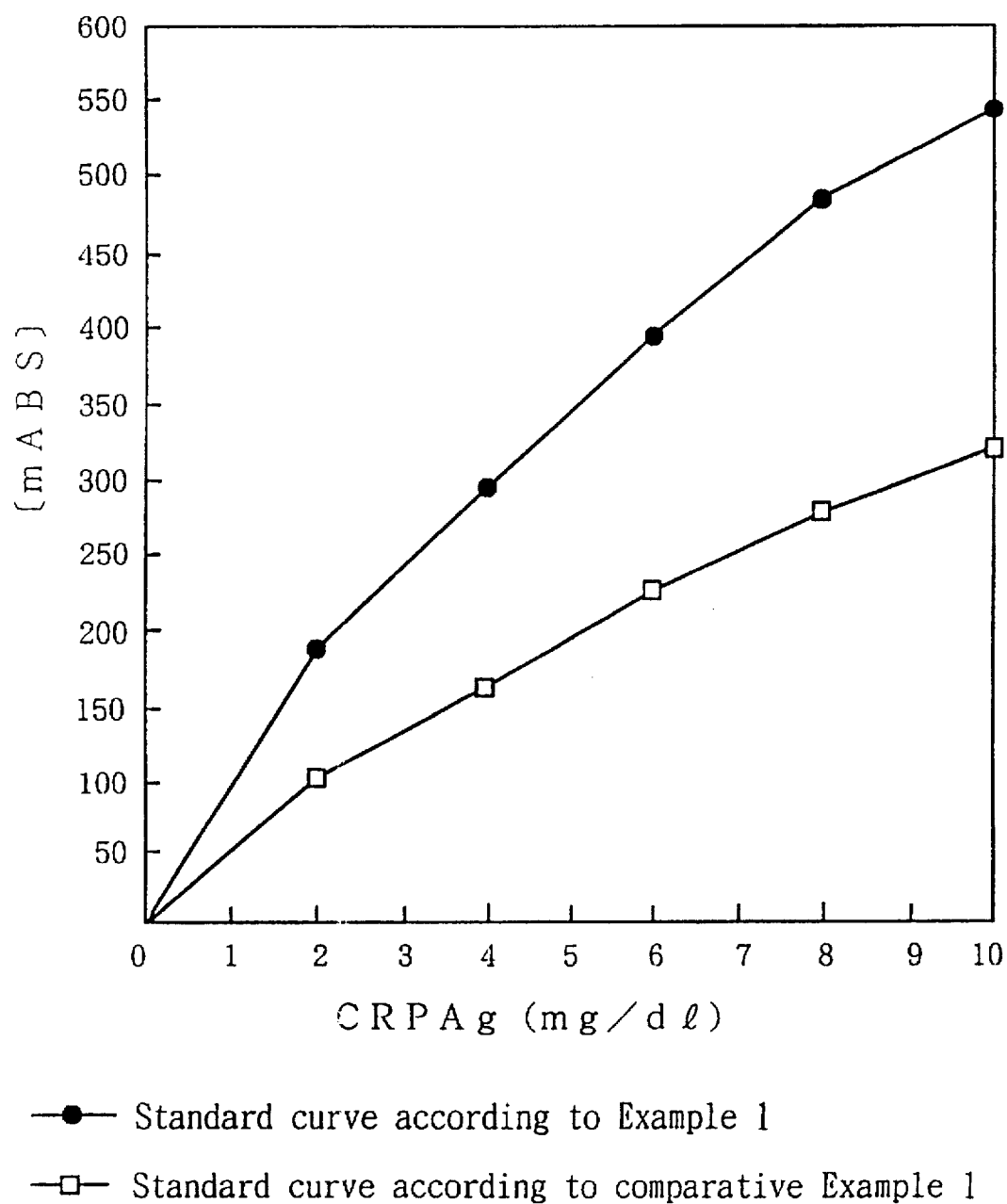
FIG. 1 shows a standard curve obtained with an immunoagglutination reagent in an CRP assay, wherein the reagent includes, as the carriers, liposomes entrapping a gelled compound and liposomes entrapping TES buffer.

In the following Example 1, an immunoagglutination reagent for CRP antigen assay by liposome turbidimetry is produced in accordance with the present invention. In Example 1, use is made of the following reagents and assay samples.

Unless otherwise stated, the same reagents and samples are used in Example 2 and Comparative Examples 1 and 2 described below.

DPPC: dipalmitoylphosphatidylcholine

Chol: cholesterol

DTP-DPPE: dithiopyridylated dipalmitoylphosphatidyl ethanolamine

Aam solution: prepared by dissolving acrylamide and Bis-acrylamide in distilled water to a final gel concentration of 2.5% and a final crosslinking degree of 5%.

TES buffer solution: prepared by dissolving TES, sodium chloride and Miracle Mornone (Trade Name of the manufacturer, Katayama Kagaku Industry Research Institute) in distilled water to final concentrations of 10 mM, 150 mM and 0.01%, respectively, and then adjusting the mixture to pH 7.5 via addition of sodium hydroxide.

Acetate buffer: prepared by dissolving acetic acid, sodium chloride, Miracle Mornone (Trade Name of the manufacturer, Katayama Kagaku Industry Research Institute) in distilled water to final concentrations of 100 mM, 150 mM and 0.01%, respectively, and then adjusting the mixture to pH 4.5 via addition of sodium hydroxide.

SPDP: N-hydroxysuccinimidyl 3-(2-pyridyldithio) propionate

DTT: dithiothreitol

Goat anti-CRP antibody: dissolved in 10 mM Hepes buffer (containing 150 mM sodium chloride, pH 7.5).

EXAMPLE 1

(A) Preparation of liposomes

A chloroform solution containing DPPC (50 µmol), Chol (50 µmol), and DTP-DPPE (2.5 µmol) is charged into a 100-ml pear-type flask, and thereafter the solution is heated to distill off the chloroform. The lipid together with the cholesterol forms a thin film on the inner wall surface of the flask. Placing the flask under reduced pressure for more than one hour, the solvent is completely distilled off.

By then adding the Aam solution (2 ml) and glass beads (2 g), followed by vigorous agitation, the thin film is peeled off. After removing the glass beads and sizing the lipid suspension to 0.2 µm by using an extruder, liposomes of a uniform particle size are prepared. The Aam solution not entrapped in the liposomes is removed by 24-hour dialysis in TES.

Ammonium persulfate (33 µl) and N,N,N',N'-tetramethylethylene diamine (14 µl) dissolved in distilled water are subsequently added to provide final individual concentrations both at 10%, for reaction at room temperature for 4 to 16 hours, whereby the entrapped Aam solution is polymerized. By removing the ammonium persulfate and N,N,N',N'-tetramethylethylene diamine after such reaction (24-hour dialysis in TES), liposomes entrapping the gelled compound are prepared. The concentration of the thus produced liposomes is determined by phosphorous assay.

(B) Introduction of a reactive group into an antibody 30 mM SPDP (10 µl; dissolved in ethanol) is added to and reacted with 10 mg/ml goat anti-CRP antibody (1 ml) at room temperature for 30 minutes. The resulting mixture is subjected to gel filtration on Sephadex G-25 equilibrated with an acetate buffer, the unreactive SPDP is removed at the time of exchange of the buffer solution. DTT is added to the resulting antibody solution to a final concentration of 10 mM for reaction at room temperature for 30 minutes. The resulting solution is then subjected to gel filtration on Sephadex G-25 equilibrated with TES. Then, DTT is removed at the time of exchange of the buffer solution. The absorbance of the resulting antibody solution is measured at 280 nm with a spectrophotometer to determine the concentration.

(C) Preparation of antibody-bearing liposomes

The liposomes prepared as described above under heading (A) (1 ml; 10 nm phosphorous concentration) are mixed and reacted with the 5 mg/ml antibody solution prepared as described above under heading (B) (1 ml), at 4° C. for 16 to 20 hours. Then, the resulting mixture is subjected to gel filtration on Sepharose CL-4B equilibrated with TES, to remove the unreacted antibody, thus isolating the liposome fraction. The phosphorous assay is conducted on the liposomes covalently coated with the resulting antibody, to determine the amount of antibody on the liposomes and to subsequently determine the amount of protein per phosphorous by the Lawry method. The particle size is determined with an analyzer of particle size distribution.

(D) Assay of CRP antigen

The liposomes covalently coated with the antibody prepared as described above under heading (C) are diluted with TES to a final phosphorous concentration of 1 mM, and the resulting solution is designated the immunoagglutination reagent. Using a HITACHI TYPE 7150 automatic system as the analyzer, and using purified CRP antigen (7 µl) and the immunoagglutination reagent (280 µl), the CRP antigen is assayed under the following assay conditions: a principal wave length of 340 nm and a secondary wave length of 700 nm at an analytical point of 24 to 50. The results are shown in FIG. 1.

In FIG. 1, the vertical axis represents the change in absorbance of each sample in mABS units. The absorbance shown in the figure is calculated by subtracting the blank of the reagent at zero concentration of the CRP antigen from the original absorbance. The horizontal axis represents the concentration of the CRP antigen in units mg/dl.

Comparative Example 1

The same procedure as in Example 1 is carried out, except for the use of TES instead of the Aam solution as in (A), and except for omission of ammonium persulfate and N,N,N',N'-tetramethylethylene diamine. The results are also shown in FIG. 1. As indicated in FIG. 1, a highly sensitive immunoagglutination reagent for CRP antigen assay can be produced by entrapping a gelled compound into liposomes, thereby increasing the refractive index. The change in absorbance resulting from the reaction of the antibody-bearing liposomes is thereby enhanced by about 1.7 fold.

The liposome used in the Example 1 and Comparative Example 1 is sensitized by an amount of about 1 mole phosphorous per 150 g.

EXAMPLE 2

Immune agglutination reagent for RF assay by liposome turbidimetry

Liposomes are prepared as described above in Example 1. Also, antigen-bearing liposomes are prepared in the same manner as in Example 1, except for the use of a heat-aggregated human IgC as an antigen, instead of the goat anti-CRP antibody. RF assay:

The antigen-sensitized liposomes prepared above are diluted with TES to a final phosphorous concentration of 0.25 mM, and the resulting solution is designated a second reagent. A first reagent is prepared by using TES. Using a HITACHI TYPE 7150 automatic system as the analyzer, and using RF-positive serum (10 μl) and the first reagent (300 μl) and the second reagent (100 μl). RF is determined using a principal wave length of 340 nm and a secondary wave length of 70n nm at an analytical point of 24 to 50. The results are shown in FIG. 2.

Figure 2:
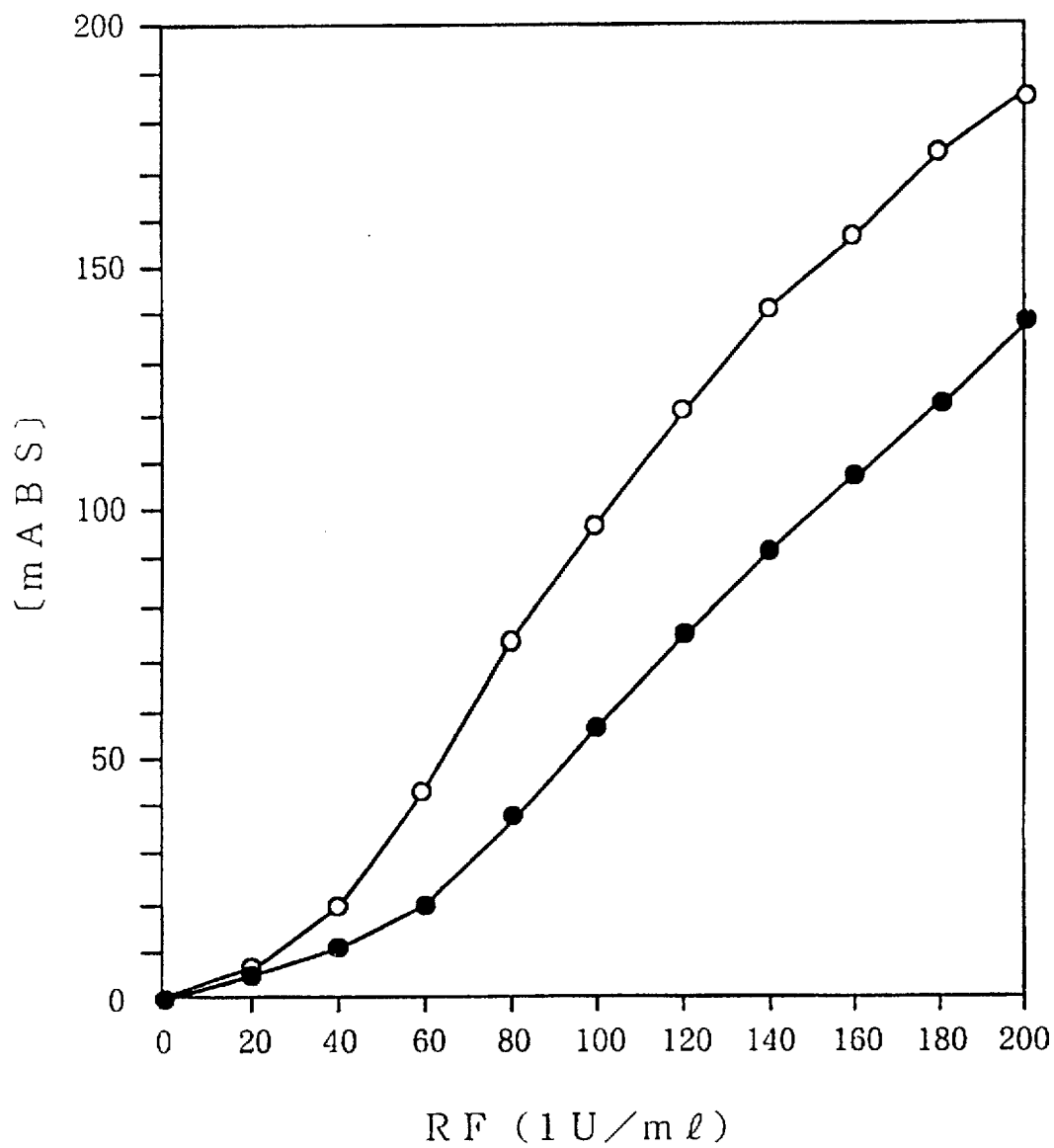
FIG. 2 shows a standard curve obtained with an immunoagglutination reagent in an RF assay, wherein the reagent includes, as the carriers, liposomes entrapping a gelled compound and liposomes entrapping TES buffer.

In FIG. 2, the vertical axis represents the change in absorbance for each sample in units mABS. The absorbance shown is calculated by subtracting the blank of the reagent at zero concentration of the RF antigen from the original absorbance. The horizontal axis represents the concentration of the RF antigen.

Comparative Example 2

Sensitizing the heat-aggregated human IgG in the same manner as in Comparative Example 1, RF is assayed in the same manner as in Example 2 (A). The results are shown in FIG. 2 which indicates that a highly sensitive RF diagnostic assay reagent can be produced by entrapping the gelled compound in liposomes to increase the refractive index. The absorbance change resulting from the liposome reaction is increased by about 1.4 fold. In Comparative Example 2, as in Example 2, about 1 mole phosphorous per 210 g is used for sensitization.

FIGS. 1 and 2 confirm that by enveloping a water-soluble polymer compound or a gelled compound into liposomes and by using such liposomes as the carrier for an immunoagglutination reagent (with the assay principal) in an agglutination reaction, the assay sensitivity can be increased.

Assaying an antigen or an antibody contained in a sample using the immunoagglutination reagent in accordance with the present invention, the change in turbidity due to the liposome agglutination via the antigen-antibody reaction can be enhanced, whereby a lower concentration of a substance in the sample can be assayed at a high sensitivity.

In accordance with the present invention, furthermore, liposomes with less antigenicity are used as the carrier. Thus, non-specific agglutination hardly occurs.

Because assaying can be done with an automatic system by means of the immunoagglutination reagent in accordance with the present invention, a great number of samples can be assayed together within a short period. Assaying can be done in a stable manner because no contamination of such automatic system occurs.

We claim:

1. An immunoagglutination reagent for use in an assay measuring a level of agglutination caused by an antigen-antibody reaction, said reagent comprising:

a carrier in the form of liposomes containing, entrapped therein, a water-soluble polymer compound or a gelled compound said entrapped compound increasing the refractive index of the liposomes wherein said entrapped compound is a polymer or copolymer selected from the group consisting of:

polymers and copolymers of acrylamide and glycosylmethacrylate;

cellulose and cellulose derivatives;

methyacrylate polymers;

acrylic acid and acrylate polymers and copolymers; and N-vinylpyrollidone polymers; and, an antibody or antigen immobilized on surfaces of said liposomes.

2. An immunoagglutination reagent according to claim 1, wherein the antibody or the antigen is covalently immobilized onto the surface of the liposome.

3. An immunoagglutination reagent according to claim 1, wherein said entrapped compound is a polymer cross-linked through a cross-linking agent.

4. An immunoanalytical method comprising contacting the immunoagglutination reagent according to claim 1 with a sample containing an antigen or antibody to be assayed to react said antigen or antibody in said sample with the immobilized antibody or antigen, and measuring the level of liposome agglutination caused by the antigen-antibody reaction as a decrease in photo-transmission.

5. A method according to claim 4 wherein said decrease in photo-transmission is observed in shortwave light at a wavelength of about 340 nm.

6. A method according to claim 4 wherein said entrapped compound is a polymer cross-linked through a cross-linking agent.

* * * * *

UNITED STATES PATENT AND TRADEMARK OFFICE
CERTIFICATE OF CORRECTION

PATENT NO. : 5,756,363
DATED : May 26, 1998
INVENTOR(S) : UENO et al

It is certified that error appears in the above-indentified patent and that said Letters Patent is hereby corrected as shown below:

In the legends of Fig. 2, "Example 1" should read --Example 2--, both instances.

Col. 8, line 10, after "liposomes" insert a comma --,--.

Signed and Sealed this

Twenty-seventh Day of April, 1999

Attest:

Q. TODD DICKINSON

*Attesting Officer*   *Acting Commissioner of Patents and Trademarks*